ically large. The column a heading lists the patent/document number, followed by issue date, first-named party, and reference page.

United States Patent [19]
Hill et al.

[11] Patent Number: 4,857,549
[45] Date of Patent: Aug. 15, 1989

[54] ANTITUMOR COMPOUNDS COMPOSITIONS AND METHODS FOR TREATING TUMORS EMPLOYING α,ω-BIS(DISUBSTITUTEDPHOSPHINO)-HYDROCARBON DERIVATIVES OR (α,ω-BIS(DISUBSTITUTEDPHOSPHINO)HYDROCARBON) DIGOLD(I), DIGOLD(III), DISILVER(I), AND DICOPPER(I)

[75] Inventors: David T. Hill, North Wales; Randall K. Johnson, Ardmore; Christopher K. Mirabelli, Malvern, all of Pa.

[73] Assignee: SmithKline Beckman Corporation, Philadelphia, Pa.

[21] Appl. No.: 160,898

[22] Filed: Feb. 26, 1988

Related U.S. Application Data

[60] Division of Ser. No. 718,905, Apr. 2, 1985, Pat. No. 4,766,226, which is a continuation-in-part of Ser. No. 685,881, Dec. 24, 1984, abandoned, which is a continuation-in-part of Ser. No. 575,650, Feb. 1, 1984, abandoned.

[51] Int. Cl.$^4$ .............................................. A61K 3/28
[52] U.S. Cl. .................................... 514/495; 514/499
[58] Field of Search .............................. 514/495, 499

[56] References Cited

U.S. PATENT DOCUMENTS

| | | | |
|---|---|---|---|
| 3,548,022 | 12/1970 | Iwamoto et al. | 556/18 |
| 3,558,520 | 1/1971 | Kubicek et al. | 556/110 |
| 3,661,959 | 5/1972 | Vaughan | 556/18 |
| 3,798,241 | 3/1974 | Kagan et al. | 556/18 |
| 4,008,281 | 2/1977 | Knowles et al. | 556/18 |

OTHER PUBLICATIONS

Weinstock et al., J. Med. Chem 7(1), 139–140 (1974).
Marsich et al., J. Inorg. Nucl. Chem 34, 933–49 (1972).
Levason et al., Inorg. Chim. Acta 8, 25–26 (1974).
Burmeister et al., Syn. Inorg. Metal, Org. Chem 2(4), 295–309 (1972).
Von Attekum et al., Inorg. Chem. 19, 701–4 (1980).
Mirabelli et al., Cancer Research 45, 32–39 (1985).
Struck et al., J. Med. Chem. 9, 414–6 (1966).
DeStefano et al., Inorg. Chem. 10, 998–1003 (1971).

*Primary Examiner*—Paul F. Shaver
*Assistant Examiner*—Stuart L. Hendrickson
*Attorney, Agent, or Firm*—Carol G. Canter; Edward T. Lentz; Alan D. Lourie

[57] ABSTRACT

Compounds, pharmaceutical compositions and a method for treating tumors by administering an effective tumor cell growth-inhibiting amount of a α,ω-bis(disubstitutedphosphino)hydrocarbon compound or a [α,ω-bis(disubstitutedphosphino)hydrocarbon] digold(I), digold(III), disiliver(I) or dicopper(I) complex to an animal afflicted by such tumor cells.

14 Claims, No Drawings

ANTITUMOR COMPOUNDS

This is a divisional of application Ser. No. 718,905 filed Apr. 2, 1985, now U.S. Pat. No. 4,766,226, which is a continuation-in-part of application Ser. No. 685,881 filed Dec. 24, 1984, which is abandoned, which is a continuation-in-part of application Ser. No. 575,650 filed Feb. 1, 1984, which is abandoned.

BACKGROUND OF THE INVENTION

This invention relates to novel α, ω-bis-(disubstitutedphosphino) hydrocarbon compounds, digold (I), digold (III), disilver (I) or dicopper (I) complexes thereof, pharmaceutical compositions containing, as an active ingredient, α,ω-bis(disubstituted-phosphino)hydrocarbon compounds or [α, ω-bis(disubstituted-phosphino)hydrocarbon] digold (I), digold (III), disilver (I) or dicopper (I) compounds which have antitumor activity. In addition, this invention relates to a method for treating tumors by administering tumor-inhibiting amounts of said active ingredient to a host animal. As disclosed more fully below, the active ingredients are cytotoxic to mammalian cells in vitro, for example B16 melanoma cells, and tumoricidal against animal tumors in vivo, for example P388 leukemia tumors.

Vaughan, U.S. Pat. No. 3,661,959, issued May 9, 1972, discloses the preparation of Au, Au'-dichloro [methylenebis(diphenylphosphine)] gold (I) (Example 21) and Au, Au'-dichloro[ethylenebis(diphenylphosphine)] for these compounds is disclosed or suggested by the Vaughan reference. Weinstock et al., *J. Med. Chem.*, 7(1), 139–140 (1974), discloses μ-[1,2-bis (diphenylphosphino) ethane] bis [chlorogold (I)] as an intermediate in the preparation of a polymeric compound, designated as Compound 5. Compound 5 was tested, but found to be ineffective as an oral antiarthritic agent. There is no disclosure or suggestion in the Weinstock reference that the intermediate has antiarthritic or any other type of pharmaceutical activity. Mc Auliffe et al., *J.C.S. Dalton*, 1730–1735 (1979), disclose physical and chemical data for several [αω-bis(disubstitutedphosphino) hydrocarbon] digold (I) compounds in Tables 1 and 4. However, there is no disclosure or suggestion in the Mc Auliffe reference that such compounds have any pharmaceutical activity. Marsich et al., *J. Inorg. Nucl. Chem.*, 34, 933–949 (1972), disclose μ-[1, 2-Bis(diphenylphosphino) ethane ] bis [chlorocopper (I)]. However, there is no disclosure or suggestion in this reference that this compound has any pharmaceutical activity. Levason et al., *Inorg. Chim. Acta*, 8, 25–26 (1974), discloses μ-[1, 2-Bis (diphenylphosphino)alkyl] bis [nitratosilver (I)] compounds, wherein alkyl is methane, ethane, propane and ethylene. However, there is no disclosure or suggestion in this reference that these compounds have any pharmaceutical activity. DeStefano et., *Inorg. Chem.*, 10, 998–1003 (1971), disclose μ-[1, 2-Bis(diphenyl-phosphino)ethane] bis[thiocyanatogold(I)]. However, there is no disclosure or suggestion in the DeStefano reference that this compound has any pharmaceutical activity. Struck et al., *J. Med. Chem.*, 9, 41–416 (1966), disclose alleged cytotoxic activity for ethylenebis(diphenylphosphine) which is the active ingredient in some of the pharmaceutical compositions and methods of treatment of the instant application, and is also used as an intermediate in the preparation of some of the metal complexes of the instant invention. However, there is no disclosure or suggestion in the Struck reference of such metal complexes, or that they would display cytotoxic or any other pharmaceutical activity.

SUMMARY OF THE INVENTION

This invention relates to a pharmaceutical composition comprising an effective tumor cell growth-inhibiting amount of an active ingredient and an inert pharmaceutically acceptable carrier or diluent, wherein said composition is useful for inhibiting the growth of animal tumor cells sensitive to the active ingredient, and wherein the active ingredient is a [αω-bis(disubstitutedphosphino)hydrocarbon] digold (I), digold (III), disilver (I), or dicopper (I) compound represented by the following general structural formula:

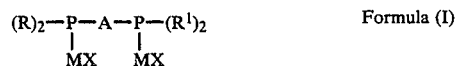   Formula (I)

in which:

R an $R^1$ are the same and are phenyl; perdeuterophenyl; cyclohexyl; benzyl; pentahalophenyl, monosubstituted phenyl wherein said substituent is selected from halogen, methoxy, methylthio or trihalomethyl; or R is ethyl provided that $R^1$ is phenyl;

A is a straight or branched alkanediyl chain of from one to six carbon atoms, cis-vinylene or trans-vinylene;

M is the same and is Au(I), Au(III), Ag(I) or Cu(I) ; and

X is the same and is halo, nitrato, $C_{1-6}$ alkylcarboxylato, thiocyanato, perfluoroalkylthio, cysteine $C_{1-6}$ alkylester or $C_{1-6}$ alkyldithiocarbanato.

This invention also relates to a pharmaceutical composition comprising an effective tumor cell growth-inhibiting amount of an active ingredient and an inert pharmaceutically acceptable carrier or diluent, wherein said composition is useful for inhibiting the growth of animal tumor cells sensitive to the active ingredient, and wherein the active ingredient is a $α\frac{ω}{β}$-bis(disubstitutedphosphino)hydrocarbon compound represented by the following general structural formula:

   Formula (IA)

in which:

$R^2$ and $R^3$ are the same and are phenyl; perdeuterophenyl; ethyl; cyclohexyl; monosubstituted phenyl wherein said substituent is selected from halogen or methylthio; or $R^2$ is ethyl provided that $R^3$ is phenyl; and $A^1$ is phenylene, a straight or branched alkanediyl chain of from one to five carbon atoms, cisvinylene, or trans-vinylene; provided that when $R^2$ and $R^3$ are the same and are phenyl, $A^1$ is other than hexane-1, 2-diyl.

This invention also relates to a method of inhibiting the growth of animal tumor cells sensitive to a Formula (I) or Formula (IA) compound which comprises administering to an animal afflicted with said tumor cells an effective tumor cell growth-inhibiting amount of a compound of Formula (I) or Formula (IA).

This invention also relates to a compound of the formula:

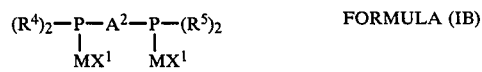   FORMULA (IB)

wherein

R⁴ and R⁵ are the same and are phenyl, perdeuterophenyl, cyclohexyl, benzyl, pentahalophenyl, monosubstituted phenyl wherein said substituent is selected from halo, methoxy, methylthio or trihalomethyl; or R⁴ is ethyl provided that R⁵ is phenyl;

$A^2$ is a straight or branched alkanediyl chain of one to six carbon atoms, cis-vinylene or trans-vinylene;

M is the same and is Au(I), Au(III), Ag(I) or Cu(I); and $X^1$ is the same and is halo, nitrato, $C_{1-6}$ alkylcarboxylato, thiocyanato, perfluoroalkylthio, $C_{1-6}$ alkyldithiocarbanato; or cysteine $C_{1-6}$ alkylester;

provided that when $R^4$ and $R^5$ are phenyl and M is Ag(I), $X^1$ is other than nitrato; and further provided that when $R^4$ and $R^5$ are phenyl, M is Ag(I) and $A^2$ is ethane-1,2-diyl, $X^1$ is other than acetato; and further provided that when $R^4$ and $R^5$ are phenyl, M is Cu(I) and $A^2$ is ethane-1,2-diyl, $X^1$ is other than chloro; and further provided that when $R^4$ and $R^5$ are phenyl and M is Au(I), $X^1$ is other than halo or thiocynato; and further provided that when $R^4$ and $R^5$ are phenyl, m is Au(III), and A is ethane-1,2-diyl, $X^1$ is other than halo or thiocyanato.

This invention also relates to a compound of the formula:

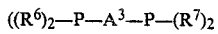

wherein $R^6$ and $R^7$ are the same and are perdeuterophenyl or monosubstituted phenyl wherein said substituent is selected from methoxy; methylthio; or halo; and $A^3$ is a straight or branched alkanediyl chain of one to six carbon atoms, cis-vinylene or trans-vinylene.

DETAILED DESCRIPTION OF THE INVENTION

One skilled in the art will recognize that all the compounds of Formula (IB) are embraced by the scope of Formula (I); and that all the compounds of Formula (IC) are embraced by the scope of Formula (IA).

The term "straight or branched alkanediyl chain of from one to six carbon atoms" is meant to include both the resolved and unresolved configurations.

Preferred compounds of Formula (I) include those wherein R and $R^1$ are the same and are phenyl, cyclohexyl, benzyl or monosubstituted phenyl wherein said substituent is selected from halo or methylthio, A is ethane-1,2-diyl, propane-1,2-diyl, propane-1,3-diyl or cis vinylene, M is gold(I), gold(III) or copper(I) and X is halo, acetato, thiocyanato or trifluoromethylthio. These compounds are preferred because they exhibit good antitumor activity in at least one in vivo tumor assay. Particularly preferred compounds of Formula (I) include those wherein R and $R^1$ are the same and are phenyl or benzyl, A is ethane-1,2-diyl, propane-1,2-diyl, propane-1,3-diyl or cis-vinylene, M is gold(I) or gold(III), and X is halo, thiocyanato, trifluoromethylthio or acetato. Especially preferred compounds of Formula (I) include those wherein R and $R^1$ are the same and are phenyl, A is ethane-1,2-diyl, M is gold(I), and X is chloro or bromo.

Preferred compounds of Formula (IA) include those wherein $R^2$ and $R^3$ are the same and are phenyl, cyclohexyl or perdeuterophenyl; and $A^1$ is ethane-1,2-diyl, propane-1,2-diyl, propane-1,3-diyl, cis-vinylene or phenylene. Particularly preferred compounds of Formula (IA) include those wherein $R^2$ and $R^3$ are the same and are phenyl, and A is ethane-1,2-diyl, propane-1,2-diyl, propane-1,3-diyl or cis-vinylene. Most preferred is the Formula (IA) compound wherein $R^2$ and $R^3$ are the same and are phenyl and $A^1$ is $(CH_2)_2$.

The active ingredients used in this invention are either known or are prepared by methods readily available to one skilled in this art. All the compounds of Formula (IA) are either available from commercial sources, for example Strem Chemicals, Inc., Danvers, Mass., or can be prepared by methods known to one skilled in this art, for example, from 1,2-bis(dichlorophosphino)ethane by reaction with a Grignard reagent derived from a $R^2$ or $R^3$ substituted halide. Generally, the starting materials needed to prepare Formula (I) compounds are the corresponding diphosphino hydrocarbons represented by the following structural formula:

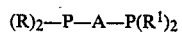

FORMULA (II)

in which R, $R^1$ and A are defined above. To obtain the digold(I) products of Formula (I) wherein X is chloro, an appropriate diphosphino hydrocarbon intermediate of Formula (II) is reacted either directly with chloroauric acid hydrate or a reduced form of the acid hydrate obtained by treatment with thiodiglycol. For example, a solution of thiodiglycol in a nonreactive organic solvent, such as methanol or ethanol, is reacted with an aqueous solution of chloroauric acid hydrate cooled to a temperature of from −10° to 0° C., and then treated with a solution of the appropriate diphosphino hydrocarbon in a nonreactive organic solvent system, such as a mixture of chloroform and methanol, for from one to two hours to give the corresponding [αω-bis(disubstitutedphosphino)hydrocarbon] bis[chlorogold(I)] derivative. Similarly, chloroauric acid hydrate in a nonreactive organic solvent, such as methanol or ethanol, is reacted with a solution of the appropriate diphosphino hydrocarbon at ambient temperature for from one to two hours to give the corresponding [αω-bis(disubstitutedphophino)hydrocarbon] bis[chlorogold(I)] derivative.

To obtain the digold (III) products of Formula (I) wherein X is trichloro, the corresponding digold(I) product wherein X is chloro is treated with chlorine gas, for example by passing chlorine through a chloroform solution, at ambient temperature until the solution is saturated.

The gold products of Formula (I) wherein X is other than chloro are conveniently prepared from the corresponding Formula (I) gold product wherein X is chloro by treatment with an appropriate salt which provides the desired anion, for example silver acetate, silver trifluoromethylthiolate, sodium bromide, sodium thiocyanate or potassium ethylxanthate, in an inert organic solvent such as methylene chloride, chloroform or dimethylformamide at ambient temperature.

To obtain the silver(I) or copper(I) products of Formula (I), an appropriate diphosphino hydrocarbon intermediate of Formula (II) above is reacted with a silver or copper salt, selected to provide the desired anion, for example silver nitrate or cuprous chloride, in an inert organic solvent such as ethanol, acetonitrile, chloroform or mixtures of such solvents, at an elevated temperature up to reflux temperature.

The starting materials represented by Formula (II) above are either available from commercial sources or prepared by methods known to one skilled in this are, for example, from 1,2-bis(dichlorophosphino)ethane by reaction substituted halide.

As stated above, the active ingredients used herein have antitumor activity as demonstrated in a variety of test systems. Initially, the cytotoxic activity of the Formula (I) and Formula (IA) compounds used in the pharmaceutical compositions and methods of treatment of the instant invention was evaluated in vitro using B16 melanoma cells according to the following assay:

B16 melanoma (highly metastatic subline, F10) are used and maintained as monolayer cultures in Minimal Essential Media (Grand Island Biological Co., Grand Island, N.Y.) supplemented with 10% calf serum, 1% antibiotics in a 5% $CO_2$ humidified incubator at 37° C. Asynchronous populations of cells are harvested and replated to 5000 cells/plate in sterile 60 mm×15 mm petri plates. Plates are incubated overnight to allow attachment of the cells to the plate. Cells are treated with a Formula (I) or Formula (IA) compound or cisplatin under sterile conditions, allowed to react for 2 hours followed by aspiration of medium. Plates are washed one time with 5 ml of phosphate buffered saline (PBS), followed by the addition of 5 ml of fresh media. Plates are incubated for 5 days at 37° in a $CO_2$ incubator. Viability is measured by the ability of a cell to form a colony of greater than 50 cells. Colonies are fixed with 0.5% crystal violet in 95% ethanol. Plates are dried and counted with a Biotran III Automatic Count Totalizer (New Brunswick Scientific Co., Edison, N.J.). Mean and standard deviation of triplicate samples are determined for each drug concentration. The data are analyzed by plotting the log of the survival fraction (number of colonies in drug treated plates/number of colonies in controls) versus the drug concentration.

A summary of the evaluation of several of the compounds of Formula (I) in the B16 melanoma in vitro assay is shown in the following Table A.

A summary of the evaluation of several of the compounds of Formula (IA) in the B16 melanoma in vitro assay is shown in the following Table AI.

TABLE AI $(R^2)_2-P-A-P-(R^3)_2$
Formula IA

| Compound[b] | $R^2$ | $R^3$ | A | $IC_{50}$[a] (uM) |
|---|---|---|---|---|
| 2 | phenyl | phenyl | $(CH_2)_2$ | 60 |
| 3 | phenyl | phenyl | CIS-CH=CH | 25 |
| 4 | phenyl | phenyl | $CH(CH_3)CH_2(RS)$ | 50 |
| 5 | phenyl | phenyl | $CH(CH_3)CH_2(R)$ | 50 |
| 6 | phenyl | phenyl | $(CH_2)_3$ | 72 |
| 9 | phenyl | phenyl |  | 28 |
| 12 | perdeuterophenyl | perdeuterophenyl | $(CH_2)_2$ | 50 |

[a] concentration which inhibits cloning efficiency of B16 melanoma cells by 50% on a 2 hour exposure.
[b] compounds numbered in accordance with the numbering designation used in Table B1.

The antitumor activity of the Formula (I) and Formula (IA) compounds used herein was evaluated in a P388 leukemia mouse model employing the following protocol:

$10^6$ P388 leukemia cells are inoculated intraperitoneally (ip) in $B6D2F_1$ mice. Twenty-four hours later, if the tumor inoculum proves to be free of bacterial contamination (as determined by 24 hours incubation in thioglycollate broth), animals are randomized into groups of 6 and housed in shoebox cages. Formula (I) or Formula (IA) compounds are dissolved in a minimal volume of either N,N-dimethylacetamide (DMA) or 95% ethanol (depending upon solubility). An equal volume of saline is added; if the drug comes out of solution an equal volume of Cremophor (polyethoxylated castor oil) is added and then saline qs to a concentration such that the desired dose is delivered in 0.5 ml. The final concentration of DMA, ethanol and Cremophor is 10 percent. Dilution for lower doses are made with saline so there is a decreasing proportion of organic solvents in the vehicle with decreasing dosage. These vehicles provide soluble formulations (or suspensions). Formulations are prepared immediately prior to injection. The Formula (I) or Formula (IA) compounds are administered ip on Days 1 through 5 (i.e. treatment is initiated 24 hrs after tumor inoculation). Each experiment includes three groups of 6 animals as untreated controls and animals treated with a positive control, cisplatin, at two dose

TABLE A $(R)_2-P-A-P-(R^1)_2$
　　　　|　　　|
　　　MX　　MX

Formula (I)

| Compound[b] | R | $R^1$ | A | M | X | $IC_{50}$[a] ($\mu$M) |
|---|---|---|---|---|---|---|
| 1 | phenyl | phenyl | $CH_2$ | Au(I) | Cl | 6 |
| 2 | phenyl | phenyl | $(CH_2)_2$ | Au(I) | Cl | 8 |
| 3 | phenyl | phenyl | $(CH_2)_3$ | Au(I) | Cl | 2 |
| 4 | phenyl | phenyl | $(CH_2)_4$ | Au(I) | Cl | 3 |
| 5 | phenyl | phenyl | $(CH_2)_5$ | Au(I) | Cl | 2 |
| 6 | phenyl | phenyl | $(CH_2)_6$ | Au(I) | Cl | 2 |
| 7 | phenyl | phenyl | CIS-CH=CH | Au(I) | Cl | 7 |
| 12 | phenyl | phenyl | $(CH_2)_2$ | Au(III) | $Cl_3$ | 4 |
| 21 | cyclohexyl | cyclohexyl | $(CH_2)_2$ | Au(I) | Cl | 14 |

[a] concentration which inhibits cloning efficiency of B16 melanoma cells by 50% on a 2-hour exposure.
[b] compounds numbered in accordance with the numbering designation used in Table B.

levels. Animals are weighed as a group on Days 1, 5 and 9 and average weight change (Δwt.) is used as a reflection of toxicity. Each experiment also includes an inoculum titration—groups of 8 mice inoculated ip with $10^5$ to $10^0$ P388 leukemia cells. The titration is used to calculated cell kill achieved by treatment with drugs. Animals are monitored daily for mortality and experiments are terminated after 45 days. The endpoint is median survival time (MST) and increase in lifespan (ILS) which is the percentage of increase in MST relative to untreated controls. Untreated controls inoculated ip with $10^6$ P388 leukemia cells generally survive for a median of 10 or 11 days. A drug is considered active if it produces an average of $\geq 25$ percent ILS.

A summary of the evaluation of Formula (I) compounds in the in vivo ip P388 model is shown in TABLE B.

A summary of the evaluation of Formula (IA) compounds in the in vivo ip P388 model is shown in Table BI.

TABLE B $$(R)_2-P-A-P-(R^1)_2$$
$$\quad\quad\quad | \quad\quad |$$
$$\quad\quad MX \quad MX$$

Formula (I)

| Compound No. | R | $R^1$ | A | M | X | $MTD^{(a)}$ (mg/kg) | $ILS^{(b)}$ (%) |
|---|---|---|---|---|---|---|---|
| 1 | phenyl | phenyl | $CH_2$ | Au(I) | Cl | 50 | 62/50 |
| 2 | phenyl | phenyl | $(CH_2)_2$ | Au(I) | Cl | 6 | $93 \pm 23^{(c)}$ |
| 3 | phenyl | phenyl | $(CH_2)_3$ | Au(I) | Cl | 8 | 60/45/44/100 |
| 4 | phenyl | phenyl | $(CH_2)_4$ | Au(I) | Cl | 6 | 45/40 |
| 5 | phenyl | phenyl | $(CH_2)_5$ | Au(I) | Cl | 4 | 55/55 |
| 6 | phenyl | phenyl | $(CH_2)_6$ | Au(I) | Cl | 4 | 40/35 |
| 7 | phenyl | phenyl | cis-CH=CH | Au(I) | Cl | 4 | 105/77 |
| 8 | phenyl | phenyl | trans-CH=CH | Au(I) | Cl | 24 | 33/36 |
| 9 | phenyl | phenyl | $CH_2(CH_3)CH(RS)$ | Au(I) | Cl | 6 | 45/60/35 |
| 10 | phenyl | phenyl | $CH_2(CH_3)CH(RS)$ | Au(I) | Cl | 6 | 50/25 |
| 11 | phenyl | phenyl | $CH(CH_3)CH(CH_3)(SS)$ | Au(I) | Cl | 6 | 73/25/35 |
| 12 | phenyl | phenyl | $(CH_2)_2$ | Au(III) | $Cl_3$ | 16 | 95/62 |
| 13 | phenyl | phenyl | $(CH_2)_2$ | Ag(I) | $NO_3$ | 6 | 45/30 |
| 14 | phenyl | phenyl | $(CH_2)_2$ | Cu(I) | Cl | 4 | 65/79 |
| 15 | phenyl | phenyl | $(CH_2)_2$ | Au(I) | Br | 12 | 116/80 |
| 16 | phenyl | phenyl | $(CH_2)_2$ | Au(I) | SCN | 6 | 36/62/45 |
| 17 | phenyl | phenyl | $(CH_2)_2$ | Au(I) | $OCOCH_3$ | 4 | 73/64 |
| 18 | phenyl | phenyl | $(CH_2)_2$ | Au(I) | $SCF_3$ | 6 | 45/86/40 |
| 19 | phenyl | phenyl | $(CH_2)_2$ | Au(I) | $SCSOCH_2CH_3$ | 6 | 77/40/35 |
| 20 | phenyl | phenyl | $(CH_2)_2$ | Au(I) | $SCH_2CH(NH_2)COOEt$ | 6 | 50/56 |
| 21 | phenyl | ethyl | $(CH_2)_2$ | Au(I) | Cl | 16 | 30/30 |
| 22 | cyclohexyl | cyclohexyl | $(CH_2)_2$ | Au(I) | Cl | 16 | 60/32/80 |
| 23 | benzyl | benzyl | $(CH_2)_2$ | Au(I) | Cl | 4 | 45/30 |
| 24 | p-methoxy-phenyl | p-methoxy-phenyl | $(CH_2)_2$ | Au(I) | Cl | 8 | 45/30/20 |
| 25 | p-fluoro-phenyl | p-fluoro-phenyl | $(CH_2)_2$ | Au(I) | Cl | 8 | 80/75 |
| 26 | m-fluoro-phenyl | m-fluoro-phenyl | $(CH_2)_2$ | Au(I) | Cl | 8 | 60/55 |
| 27 | pentafluoro-phenyl | penta-fluorophenyl | $(CH_2)_2$ | Au(I) | Cl | 16 | 30/25 |
| 28 | o-methylthio-phenyl | o-methylthio-phenyl | $(CH_2)_2$ | A(I) | Cl | 8 | 35/126/50 |
| 29 | p-trifluoro-methylphenyl | p-trifluoro-methylphenyl | $(CH_2)_2$ | Au(I) | Cl | 8 | 37/44 |
| 30 | p-methylthio-phenyl | p-methylthio-phenyl | $(CH_2)_2$ | Au(I) | Cl | 8 | 37/65 |
| 31 | perdeutero-phenyl | perdeutero-phenyl | $(CH_2)_2$ | Au(I) | Cl | 6 | 40/65 |

[a] maximally tolerated dose for $B6D2F_1$ female mice on an ip qD $\times$ 5 regimen.
[b] maximum increase in lifespan produced in mice bearing ip P388 leukemia (figures separated by a slash were generated in separate experiments).
[c] Figure based on data generated in 35 separate experiments.

TABLE BI $$(R^2)_2-P-A^1-P-(R^3)_2$$

FORMULA (IA)

| COMPOUND NO. | $R^2$ | $R^3$ | $A^1$ | $MTD^{(a)}$ (mg/kg) | $ILS^{(b)}$ (%) |
|---|---|---|---|---|---|
| 32 | phenyl | phenyl | $CH_2$ | 256 | 40/40 |
| 33 | phenyl | phenyl | $(CH_2)_2$ | 16 | $98 \pm 26^{(c)}$ |
| 34 | phenyl | phenyl | cis-CH=CH | 24 | 60/70 |
| 35 | phenyl | phenyl | $CH_2(CH_3)CH(RS)$ | 32 | 90/85/95 |
| 36 | phenyl | phenyl | $CH_2(CH_3)CH(R)$ | 32 | 100/60 |
| 37 | phenyl | phenyl | $(CH_2)_3$ | 32 | 75/65 |
| 38 | phenyl | phenyl | $(CH_2)_4$ | 28 | 45/55 |
| 39 | phenyl | phenyl | $(CH_2)_5$ | 8 | 50/40 |

TABLE BI-continued $(R^2)_2-P-A^1-P-(R^3)_2$
FORMULA (IA)

| COMPOUND NO. | $R^2$ | $R^3$ | $A^1$ | MTD[a] (mg/kg) | ILS[b] (%) |
|---|---|---|---|---|---|
| 40 | phenyl | phenyl |  | 32 | 70/55 |
| 41 | phenyl | phenyl | trans-CH=CH | 128 | 25/55 |
| 42 | phenyl | phenyl | CH(CH$_3$)CH(CH$_3$) | 48 | 73/40 |
| 43 | perdeuterophenyl | perdeuterophenyl | (CH$_2$)$_2$ | 24 | 80/95 |
| 44 | cyclohexyl | cyclohexyl | (CH$_2$)$_2$ | 32 | 80/68 |
| 45 | 4-fluorophenyl | 4-fluorophenyl | (CH$_2$)$_2$ | 8 | 60/55 |
| 46 | 3-fluorophenyl | 3-fluorophenyl | (CH$_2$)$_2$ | 32 | 45/65 |
| 47 | 2-methylthiophenyl | 2-methylthiophenyl | (CH$_2$)$_2$ | 64 | 47/83/24 |
| 48 | 4-methylthiophenyl | 4-methylthiophenyl | (CH$_2$)$_2$ | 32 | 58/35 |
| 49 | ethyl | ethyl | (CH$_2$)$_2$ | 64 | 25/30 |
| 50 | ethyl | ethyl | (CH$_2$)$_2$ | 128 | 55 |

[a]maximally tolerated dose for B6D2F$_1$ female mice on an ip qD × 5 regimen.
[b]maximum increase in lifespan produced in mice bearing ip P388 leukemia (figures separated by a slash were generated in separate experiments).
[c]Figure based on data generated in 41 separate experiments.

Another chemosensitive tumor model is intraperitoneally (ip) implanted M5076 reticulum cell sarcoma in mice. In this system B6D2F$_1$ female mice are inoculated with 0.5 ml of a 10 percent weight:volume (w:v) brei of M5076 prepared from pooled subcutaneous (sc) tumors excised at about 21 days from c57B1/6 donor mice. Drugs are administered ip. Daily treatment is begun 24 hours after implantation and is continued for ten days. The treatment regimen for M5076 is more prolonged than for P388 because of the slower growth rate and longer control survival time of the M5076 tumor. The positive control compound, cisplatin, was active in all experiments in ip M5076. A drug is considered active if it produces an average of ≧25 percent ILS. TABLE C represents data developed on the activity of several compounds of Formula (I) in the M5076 reticulum sarcoma assay. TABLE D represents data developed on the activity of several compounds of Formula (IA) in the M5076 reticulum sarcoma assay.

TABLE C

| Compound No.[a] | MTD(mg/kg)[b] | ILS max (%)[c] |
|---|---|---|
| 2 | 4 | 76 ± 30[d] |
| 7 | 3 | 90 |
| 12 | 8 | 74 |
| 3 | 5 | 69 |
| 9 | 5 | 98 |
| 15 | 12 | 69 |
| 22 | 8 | 27 |
| 16 | 5 | 52 |
| 17 | 4 | 54/67 |
| 18 | 6 | 70 |
| 23 | 4 | 40 |

[a]see TABLE B for structures
[b]maximally tolerated dose for B6D2F$_1$ female mice or an ip qD × 10 regimen.
[c]maximum increase in lifespan produced in mice bearing ip M5076 sarcoma (figures separated by a slash were generated in separate experiments).
[d]represents data generated in seven separate experiments.

TABLE D

| Compound No.[a] | MTD (mg/kg)[b] | ILS max (%)[c] |
|---|---|---|
| 33 | 6 | 70/96/68 |
| 34 | 5 | 57 |
| 35 | 24 | 62 |

[a]see TABLE BI for structures.
[b]maximally tolerated dose for B6D2F$_1$, female mice on an ip qD × 10 regimen.
[c]maximum increase in lifespan produced in mice bearing ip M5076 sarcoma (figures separated by a slash were generated in separate experiments).

Based on the data set forth in Tables C and D, the compounds of Formula (I) numbered as Compounds 2, 7, 12, 3, 9, 15, 22, 16, 18 and 17 herein have good activity in the ip M5076 reticulum cell sarcoma assay. Based on the data set forth in Table D, the compounds of Formula (IA) numbered as Compounds 33, 34 and 35 herein have good activity in the ip M5076 reticulum cell sarcoma assay.

The cytotoxic activity of Compound No. 2 from TABLE A, namely μ-[1,2-bis (diphenylphosphino)ethane]bis-[chlorogold (I)], was also determined in a human tumor cloning assay. This procedure is described as follows:

Tumor Specimens: Specimens were collected using aseptic technique and transported in medium containing Penicillin, Streptomycin, and Amphotericin B. Specimens which could not be immediately processed were minced into fragments 5 mm$^3$ or smaller, prior to transport. Effusions were collected with ten units of preservative free heparin per ml of effusion. Specimens were processed to obtain cell suspensions as soon as possible after removal from the patient.

Culture Methods: A two-layer soft agar culture system was used in these studies. [Salmon, et al., *N. Engl. J. Med.*, 298:1321 (1978)]. Cell counts were performed on a hemacytometer after lysis of erythrocytes in acetic acid. A total of 500,000 nucleated cells were plated in a volume of 1 ml (0.3 percent agar) over 1 ml base layers (0.6 percent agar) in each culture. Cultures were incubated in humidified 37° C. incubators with an atmosphere of 5 percent CO$_2$ in air and control plates monitored for growth using an inverted microscope. At the time of maximum colony formation (7–21 days in culture) final colony counts were obtained with a Bausch and Lomb FAS II image analysis system. Objects presenting a circular profile in two dimensions with a minimum diameter of 60 μm were scored as colonies by the system.

Drug Treatment: A total of six untreated or vehicle treated cultures were plated for determination of control growth in each experiment. Cultures for measurement of drug effects were plated in triplicate with the test compound incorporated into top (cellular) layer with various concentrations. For an assay to be considered completed, at least three control and two drug treated plates had to be available for counting at the termination of the experiment.

Data Collection and Analysis: Patient demographic and experimental data were collected on floppy disks integral to the image analysis system. Drug effects were expressed in terms of fractional survival, obtained by dividing the mean number of colonies observed in the treated plates by the mean number observed in the appropriate control plates.

TABLE 1 summarizes the overall in vitro activity, that is ≦50% survival of tumor colony forming units and ≦30% survival of tumor colony forming units, in the above assay for Compound No. 2 solubilized in dimethyl sulfoxide and tested at 10 μg/ml as a continuous exposure.

TABLE 1

|  | # responses ≦50%/ # evaluable (%) | # responses ≦30%/ # evaluable (%) |
|---|---|---|
| Compound No. 2 | 11/19 (58%) | 6/19 (32%) |

TABLE 2 is a direct comparison of the in vitro activity by tumor type and TABLE 3 is a summary by tumor type.

TABLE 2

| Spec # | Tumor Type | % Survival with Compound No. 2 |
|---|---|---|
| 9334 | Ovary | 88 |
| 9199 | Ovary | 11 |
| 9235 | Ovary | 30 |
| 9420 | Ovary | 15 |
| 9186 | Ovary | 103 |
| 9432 | Ovary | 36 |
| 9392 | Breast | 80 |
| 9390 | Breast | 0 |
| 9353 | Breast | 75 |
| 9244 | Lung | 78 |
| 9338 | Lung | 59 |
| 9364 | Lung | 38 |
| 9328 | Unknown primary | 77 |
| 9380 | Unknown primary | 7 |
| 9398 | Unknown primary | 32 |
| 9196 | Kidney | 45 |
| 9340 | Kidney | 45 |
| 9176 | Corpus uterus | 18 |
| 9192 | Melanoma | 58 |

TABLE 3

| Tumor Type | # responses*/# evaluable Compound No. 2 |
|---|---|
| Ovary | 4/6 |
| Breast | ⅓ |
| Lung | ⅓ |
| Unknown primary | ⅔ |
| Kidney | 2/2 |
| Corpus uterus | 1/1 |
| Melanoma | 0/1 |
| TOTALS | 11/19 (58%) |

*≦50% survival of tumor colony forming units

Based on the data from testing in the human tumor cloning system, Compound No. 2 demonstrates substantial in vitro cytotoxic activity against primary human tumor cells.

The cytotoxic activity of several compounds of Formula (I) was evaluated in vivo using B16 melanoma cells according to the following assay:

In this system, groups of eight B6D2F$_1$ mice are inoculated ip with 0.5 ml of a 10% (w:v) brei of B16 melanoma prepared from pooled sc tumors excised at 14≠21 days from C67B$_1$/6 donor mice. Daily treatment is begun 24 hours after tumor implantation and is continued daily for 10 days. The route of drug administration is ip. The mice are monitored daily for survival for 60 days. Antitumor activity is assessed by prolongation of median survival time. An ILS of ≧25% indicates activity in this tumor model.

A summary of the evaluation of several of the compounds of Formula (I) in the in vivo ip B16 melanoma assay is shown in TABLE E.

TABLE E

| Compound No.[c] | MTD(um/kg)[a] | ILS (%)[b] |
|---|---|---|
| 2 | 5 | 62/30/15 |
| 15 | 13 | 49/41 |

[a] maximally tolerated dose for B6D2F$_1$ mice on an ip qD × 10 regimen.
[b] maximum increase in lifespan produced in mice bearing ip B16 melanoma (figures separated by a slash were generated in separate experiments).
[c] see TABLE B for structures.

In addition, Compound No. 2 from Table BI was tested in the in vivo ip B16 melanoma assay and exhibited an ILS of 64, 49 and 39% at a MTD of 5 mg/kg in three separate experiments.

The anti-tumor activity of several compounds of Formula (I) was tested in a further in vivo tumor model, mammary adenocarcinoma 16/c, a tumor model sensitive to DNA binders and alkylating agents, according to the following protocol:

The mammary adenocarcinoma 16/c tumor is implanted sc in C3H mice, and the Formula (I) compound is administered ip on days 1, 5, 9, 13 and 17. Tumors are measured 3 weeks after implantation, and activity is assessed by degree of tumor growth inhibition. Cisplantin, a drug which generally produces complete inhibition of the growth of mammary adenocarcinoma 16/c, is used as a positive control. A tumor growth inhibition of ≧75% indicates that the compound is active in this type of animal tumor model.

The results of the mammary adenocarcinoma 16/c assay are summarized in TABLE F.

TABLE F

| Compound No.[a] | MTD(um/kg)[b] | Inhibition (%) |
|---|---|---|
| 2 | 9 | 91/96/39 |
| 15 | 26 | 79 |

[a] see TABLE B for structure.
[b] maximally tolerated dose for C3H mice on an intermittent ip regimen
[c] tumor growth inhibition produced in mice bearing SC mammary adenocarcinoma 16/c (figures separated by a slash were generated in separate experiments)

In addition, Compound No. 33 from TABLE BI was tested in the sc mammary adenocarcinoma 16/c assay and (i) exhibited tumor growth inhibition of 74, 43 and 97% at a MTD of 30 mg/kg when administered ip; and (ii) exhibited tumor inhibition of 95% at a MTD of 32 mg/kg when administered iv.

Likewise, Compound No. 2 from TABLE B was tested in an additional in vivo tumor model known as ADJ-PC6 Plasmactoma according to the following assay:

Tumor cells are carried by serial sc passage in BALB/c female mice and then collected aseptically on ca. Day 21 and minced in Hank's balanced salt solution. The cells are then dispersed by homogenization in a loose-fitting teflon glass homogenizer, and cell concentration is adjusted to $4 \times 10^6$ viable (trypsin blue-excluding) cells per ml by hemocytometer counts. A total of 0.5 ml ($2 \times 10^6$ cells) is implanted sc on the right flank of BALB/c female mice in groups of 8. Treatment is given ip on Days 1-10, and tumors are measured in perpendicular diameters with a vernier caliper on Day 18. Generally, $\geq 75\%$ inhibition of tumor growth reflects significant antitumor effect. Cisplatin, the positive control compound, produces complete tumor growth inhibition.

The results of the ADJ-PC6 plasmacytoma assay are summarized in Table G.

TABLE G

| Compound No.[a] | MTD (uM/kg)[b] | % Inhibition[c] |
|---|---|---|
| 2 | 7 | 96/93 |

[a]see Table B for structure
[b]maximally tolerated dose for BALB/c female mice on an ip qD × 10 regimen
[c]≤75% inhibition of tumor growth reflects significant antitumor effect (figures separated by a slash were generated in separate experiments)

Based on the data in Table G, Compound No. 2 displays excellent antitumor activity in ADJ-PC6Plasmacytoma. In addition, Compound No. 33 from TABLE BI was tested in the in vivo ip ADJ-PC6 Plasmacytoma tumor model and exhibited tumor growth inhibition of 94% at a MTD of 6 mg/kg in one experiment, and 49% at a MTD of 4 mg/kg in a second experiment.

Additionally, Compound No. 2 from Table BI was tested in the ip Lewis Lung tumor assay and exhibited an ILS of 69% at a MTD of 12 mg/kg when administered on a q4Dx4 regimen. A compound is considered active in the ip Lewis Lung tumor assay if it has an ILS of $\geq 25\%$. The protocol for carrying out this tumor assay is well known to those of skill in the art.

Additionally, Compound No. 2 from TABLE BI was tested in the ip Madison 109 lung carcinoma tumor assay and exhibited an ILS of 50% at a MTD of 16 mg/kg when administered on a q4D×4 regimen. A compound is considered active in the ip Madison 109 carcinoma assay if it has an ILS of $\geq 25\%$. The protocol for carrying out this tumor assay is well known to those of skill in the art.

The pharmaceutical compositions of this invention comprise an effective tumor cell growth-inhibiting amount of a compound of Formula (I) or Formula (IA) and an inert pharmaceutically acceptable carrier or diluent. These compositions are prepared in dosage unit form appropriate for parenteral administration.

Compositions according to the invention for parenteral administration include sterile aqueous or non-aqueous solutions, suspensions or emulsions. The composition may be in the form of a solution of the active ingredient in a minimal volume of dimethylacetamide or ethanol, for example 5% w/v, brought up to volume with peanut oil or normal saline solution. Polyethoxylated castor oil, for example 2 to 5% w/v, may also be used to solubilize the active ingredient. In addition, the composition may be in the form of a slurry with, for example, hydroxypropyl cellulose or other suitable suspending agent. As an emulsifying agent, lecithin for example may be used. The composition may also be provided in the form of a sterile solid which can be dissolved in a sterile injectable medium immediately before use.

It will be appreciated that the actual preferred dosages of the Formula (I) or Formula (IA) compounds used in the compositions of this invention will vary according to the particular complex being used, the particular composition formulated, the mode of administration and the particular site, host and disease being treated. Optimal dosages for a given set of conditions can be ascertained by those skilled in the art using conventional dosage determination tests in view of the above experimental data. For parenteral administration the dose generally employed is from about 5 mg to about 20 mg/m² of body surface per day for one to five days, repeated about every fourth week for four courses of treatment.

The method for inhibiting the growth of animal tumor cells sensitive to a compound of Formula (I) or Formula (IA) in accordance with this invention comprises administering to a host animal afflicted with said tumor cells an effective tumor cell growth-inhibiting amount of a compound of Formula (I) or Formula (IA). As described above, during the course of treatment the active ingredient will be administered parenterally in an amount selected from about 300 to about 1000 mg.

The following examples illustrate the chemical preparation of the Formula (I) and Formula (IA) compounds used in the compositions and methods of this invention, and as such are not to be construed as limiting the scope thereof. All temperatures are in degrees Centigrade.

EXAMPLE 1

μ-[1,2-Bis(Diphenylphosphino)Ethane]Bis[Chlorogold(I)]

Chloroauric acid hydrate (1.6 g, 3.8 mmol) in ethanol (20 ml) was added to bis (1,2-diphenylphosphino)ethane (1.83 g, 4.5 mmol), obtained from Strem Chemical Company, in 1:1 chloroform/ethanol (40 ml) maintained at room temperature. After one hour the white precipitate was collected, dissolved in methylene chloride, filtered and ethanol added to induce precipitation. After standing, the product was collected and dried to give 0.97 g (50%) of the named gold complex which had a melting point of 291°-293°.

EXAMPLE 2

μ-[1,3-Bis(Diphenylphosphino)Methane]Bis[Chlorogold(I)]

Thiodiglycol (2.44 g, 20 mmol) in methanol (10 ml) was added to a solution of chloroauric acid hydrate (1.0 g, 2.4 mmol) in water (20 ml) maintained at 0°. Bis(diphenylphosphino)methane (0.47 g, 1.22 mmol), obtained from Strem Chemicals Inc., Danvers, Mass., in 2:3 chloroform/methanol (50 ml) was added and the mixture stirred for one hour. Water was added and the reaction mixture extracted with chloroform. The extract was dried over sodium sulfate, filtered and the solvent removed in vacuo. The residue was dissolved in chloroform and diluted with ethanol to induce crystallization. After standing the product was collected and dried to give 0.44 g (43%) of the named gold complex which had a melting point of 271°-272°.

EXAMPLE 3

μ-[1,3-Bis(Diphenylphosphino)Propane]Bis[-Chlorogold(I)]

Chloroauric acid hydrate (1.0 g, 2.4 mmol) was reduced by thiodiglycol as in Example 2 and bis(1,3-diphenylphosphino)propane (0.5 g, 1.2 mmol), obtained from Strem Chemicals Inc., Danvers, Mass., in 1:5 chloroform/ethanol (12ml) was added at 0°. The reaction mixture was stirred for one hour. Water was added and the mixture extracted with chloroform. The extract was washed with water, dried, filtered and the solvent removed under reduced pressure. The residue was dissolved in methylene chloride, filtered, ethanol added and the solution cooled to −20°. The product was collected, washed (ethanol) and dried in air to give 0.98 g (92%) of the named gold complex which had a melting point of 256°–257°.

EXAMPLE 4

μ-[1,4-Bis(Diphenylphosphino)Butane]Bis[-Chlorogold(I)]

Bis(1,4-diphenylphosphino)butane (1.29 g, 3.0 mmol), obtained from Strem Chemicals Inc., Danvers, Mass., in 3:2 chloroform/methanol (50ml) was added to a solution of reduced chlorauric acid hydrate (from 2.5 g, 6.1 mmol as in Example 2) in 1:2 methanol/water (30 ml) maintained at 0°. Water was added and the mixture was extracted with chloroform, dried, filtered and the solvent removed in vacuo. The residue was dissolved in methylene chloride and ethanol was added. The crystallized product was collected, washed with ethanol and air dried to give 2.54 g (94%) of the named gold complex which had a melting point of 257°–259°.

EXAMPLE 5

μ-[1,5-Bis(Diphenylphospinio)Pentane]Bis[-Chlorogold(I)]

Bis (1,5-diphenylphosphino)pentane (1.06 g, 2.43 mmol), obtained from Strem Chemicals Inc., Danvers, Mass., in 1:1 chloroform/methanol (40 ml) was added to reduced chloroauric acid hydrate (2.0 g, 4.8 mmol), the reaction mixture stirred for one hour and worked up as in Examples 3 and 4. Crystallization from methylene chloride/ethanol gave 1.23 g (56%) of the named gold complex which had a melting point of 94°.

EXAMPLE 6

μ-[1,6-Bis(Diphenylphosphino)Hexane]Bis[-Chlorogold(I)]

Addition of bis (1,6-diphenylphosphino)hexane (1.1 g, 2.43 mmol), obtained from Strem Chemicals Inc., Danvers, Mass., in 2:1 chloroform/methanol (60 ml) to reduced chloroauric acid hydrate (2.0 g, 4.85 mmol) in 1:2 methanol/water (30 ml) followed by workup as in Examples 3 and 4 and crystallization from methylene chloride/ether gave 2.0 g (90%) of the named gold complex which had a melting point of 201°–202°.

EXAMPLE 7

μ-[1,2-Bis(Dicyclohexylphosphino)Ethane]Bis[-Chlorogold(I)]

Thiodiglycol-reduced chloroauric acid hydrate (2.5 g, 6.1 mmol) in 1:2 water/methanol (60 ml) and 1,2-bis(-dicyclohexylphosphino)ethane (1.28 g, 3.0 mmol), obtained from Strem Chemicals Inc., Danvers, Mass., followed by workup as in Examples 3 and 4, and crystallization from methylene chloride/ethanol gave 2.0 g (75%) of the named gold complex which had a melting point of 278°–280°.

EXAMPLE 8

μ-[1,2-Bis(Diphenylphosphino)Ethane]Bis[Trichlorogold(III)]

Chlorine gas was passed through a chloroform solution (100 ml) of μ-[1,2bis(diphenylphosphino)-ethane]bis[chlorogold(I)] (0.23 g, 0.26 mmol), prepared as described in Example 1, maintained at room temperature until the solution was saturated. The solvent was removed in vacuo, the residue treated with chloroform and filtered to give 0.18 g (69%) of the named gold complex which had a melting point of 192°, dec.

EXAMPLE 9

μ-[Cis-1,2-Bis(Diphenylphosphino)Ethylene]Bis[-Chlorogold(I)]

Chloroauric acid hydrate (1.8 g, 4.5 mmol) was reduced as described in Example 2, cis-bis(1,2-diphenylphosphino)ethylene (1.0 g, 2.5 mmol), obtained from Strem Chemicals Inc., Danvers, Mass., in 1:1 chloroform/ethanol (20 ml) was added, and the reaction mixture stirred for one hour. Ethanol (50 ml) was added and the mixture extracted with chloroform, the extract dried, filtered and the solvent removed in vacuo. The residue was recrystallized from chloroform/ether to give 1.3 g (61%) of the named gold complex which had a melting point of 240°–242°.

EXAMPLE 10

μ-[1,2-Bis(Diphenylphosphino)Propane]Bis[-Chlorogold(I)]

Thiodiglycol (1.0 g, 8.2 mmole) in methanol (10 ml) was added to chloroauric acid tetrahydrate (1.0 g, 2.43 mmole) in water (20 ml) kept at 0°. Bis(1,2-diphenylphosphino)propane (0.5 g, 1.22 mmole), obtained from Strem Chemicals Inc., Danvers, Mass., in chloroform (20 ml)/methanol (10 ml) was added dropwise to the colorless solution. After 30 minutes, water (50 ml) was added and the mixture extracted with chloroform. The chloroform extract was washed with water, dried ($MgSO_4$), and the solvent removed in vacuo. The residue was dissolved in methylene chloride, filtered and the solvent removed in vacuo to give 1.054 g (97%) of the named gold complex as an amorphous white solid; $[\alpha]_D^{25}$ (1% $CHCl_3$)—0.5°.

EXAMPLE 11

μ-[(R)-(+)-1,2Bis(Diphenylphosphino)Propane]Bis[-Chlorogold(I)]

Using substantially the same procedure as described in Example 10, but instead using R-(+)-bis(1,2-diphenylphosphino)propane [(R)-PROPHOS], obtained from Strem Chemicals Inc., Danvers, Mass., as the disubstitutedphosphino hydrocarbon, gave 0.81 g (89%) of the named gold complex as a white sold which had a melting point of 145°, dec; $[\alpha]_D^{25}$ (1% $CHCl_3$)—29.2°.

EXAMPLE 12

μ-[Trans-1,2-Bis(Diphenylphosphino)Ethylene]Bis[-Chlorogold(I)]

Chloroauric acid tetrahydrate (3.2 g, 5 mmole) in water (50 ml) was reduced with thiodiglycol (2.93 g, 24 mmole) in water (20 ml) in standard fashion. Trans-bis(1,2-diphenylphosphino)ethylene (1.59 g, 4 mmole), obtained from Strem Chemicals Inc., Danvers, Mass., in ethanol (10 ml)/chloroform (20 ml) was added followed by the addition of ethanol (50 ml). After 1 hour, the solid was collected washed with ethanol and water, and dried to give 3.25 g of product. Extraction with chloroform followed by solvent removal gave 2.0 g (58%) of the named gold complex which had a melting point of 290°–291°.

EXAMPLE 13

μ-[(−)(2S,3S)-2,3-Bis(Diphenylphosphino)Butane]Bis[-Chlorogold(I)]

Thiodiglycol (1.6 g, 13.2 mmole) in ethanol (10 ml) was added to chloroauric acid tetrahydrate (1 g, 4,49 mmole) in water (20 ml) kept at 0°, and stirred until colorless. (−)(2S,3S)-Bis(diphenylphosphino)butane (1 g, 2.34 mmole), obtained from Strem Chemicals Inc., Danvers, Mass., in ethanol (2 ml)/methylene chloride (3 ml) was then added and the mixture stirred to ambient temperature. The precipitate was collected, washed with water, dried and recrystallized from methanol-methylene chloride to give 0.54 g (26%) of the named gold complex which had a melting point of 269°–271°; $[\alpha]_D^{25}$(1,CHCl$_3$)—23.7°.

EXAMPLE 14

μ-[1,2-Bis[Bis(4-Methoxyphenyl)Phosphino]Ethane]-Chlorogold(I)]

a. 1,2-Ethanediyl-bis[bis(4-methoxyphenyl)phosphine]

A Grignard reagent was prepared in 250 ml of dry THF from 5.83 g (0.24 g/atom) of magnesium and 44.9 g (0.24 mol) of 4-bromoanisole. The stirred mixture, under dry argon, was cooled in an ice bath as 9.27 g (0.04 mol) of 1.2-bis(dichlorophosphino)ethane, obtained from Strem Chemicals Inc., Danvers, Mass., in 50 ml of dry THF was added dropwise at such a rate that the reaction temperature did not exceed 25°. Afterwards the reaction mixture was allowed to warm to room temperature and was stirred overnight. It was then poured into a mixture of 100 ml of a saturated solution of ammonium chloride and ice, and the combined mixture was then filtered. Then the organic layer was separated and concentrated under reduced pressure to a thick syrup. The syrup was stirred with cold isopropanol and the solid was collected by filtration from isopropanol and yielded 16 g (76%) of the named product which had a melting point of 108°–110°.

b. μ-[1,2-Bis[Bis(4-methoxyphenyl)phosphino]ethane]-bis[chlorogold(I)]

A solution of 4.52 g (0.011 mol) of chloroauric acid tetrahydrate in 8 ml of distilled water was cooled in ice and treated with 4.88 g (0.04 mol) of thiodiglycol. When reduction of gold(III) to gold(I) was complete (colorless solution), 2.59 g (0.005 mol) of 1,2-ethanediylbis[-bis(4-methoxyphenyl)phosphine], prepared as described in part a, in 50 ml of acetone was added thereto. The resulting yellow solution was concentrated under reduced pressure to a semi-solid. The semi-solid was slurried with ETOH, and the named product was collected as a solid by recrystallization from acetone/ETOH, and had a melting point of 205.5°–206.5°.

EXAMPLE 15

μ-[1,2-Bis[Bis(2,3,4,5,6-Pentafluorophenyl)Phosphine]Ethane]Bis[ a. 1,2-Ethanediyl-bis[bis(2,3,4,5,6-pentafluorophenyl)-phosphine]

A solution of 11.11 g (0.045 mol) of bromopentafluorobenzene in 110 ml of dry ether was added dropwise to 15.38 ml of hexane containing 2.56 g (0.04 mol) of butyl lithium, and then cooled in dry ice under dry argon. After the halogen metal interchange was complete (Gilman Color Test I and II), a solution of 2.32 g of 1,2-bis(dichlorophosphino)ethane, obtained from Strem Chemicals Inc., Danvers, Mass., in 50 ml of dry ether was added dropwise to the cooled mixture. The mixture was then allowed to warm, and was stirred at room temperature for one hour before being treated with 50 ml of saturated ammonium chloride solution. Solid was collected from the ethereal supernatant and yielded 3.98 g (53%) of the named product from acetone with a melting point of 190°–191°.

b. μ-[1,2-Bis[bis(2,3,4,5,6-pentafluorophenyl)phosphine]ethane]-bis[chlorogold(I)]

A solution of 2.39 g (0.0058 mol) of chloroauric acid tetrahydrate in 7 ml of distilled water/25 ml acetone was stirred with 2.44 g (0.02 mol) of thiodiglycol until reduction of gold(III) to gold(I) was complete (colorless solution). The solution was cooled in ice as a warm solution of 2.00 g (0.00264 mol) of 1,2-ethanediyl-bis[-bis-(2,3,4,5,6-pentafluorophenyl)phosphine], prepared as described in part a, in 150 ml acetone was added thereto. The mixture was stirred for one hour and the named product was collected as a solid by recrystallization from acetone/ETOH, and had a melting point of 242°–244°.

EXAMPLE 16

μ-[1,2-Bis[Bis(2-Methylthiophenyl)Phosphino]Ethane]-Bis[Chlorogold(I)]

a. 1,2-ethanediyl-bis[bis(2-methylthiophenyl)phosphine]

The named product was prepared in a manner similar to the named product of Example 14a, except that 2-methylthiophenyl magnesium bromide was substituted for the magnesium and 4-bromoanisole. The named product was collected as a solid by recrystallization from CHCl$_3$/ETOH and had a melting point of 213°–216°.

b. μ-[1,2-Bis[bis(2-methylthiophenyl)phosphino]ethane]-bis[chlorogold(I)]

The named product was prepared in a manner similar to the named product of Example 15b, except that 1,2-ethanediyl-bis[bis(2-methylthiophenyl)phosphine], prepared as described in part a, was employed as the ligand. The named product was collected as a solid by recrystallization from CHCl₃/ETOH, and had a melting point of 262°-263°.

EXAMPLE 17

μ-[1,2-Bis[Bis(4-Fluorophenyl)Phosphino]Ethane]Bis-[Chlorogold (I)]

a. 1,2-ethanediyl-bis[bis(4-fluorophenyl)phosphine]

The named product was prepared in a manner similar to the named product of Example 14a, except that 4-fluorophenyl magnesium bromide was substituted for the magnesium and 4-bromoanisole. The named product was collected as a solid by recrystallization from ETOH and had a melting point of 132°-133°.

b. μ-[1,2-Bis[(4-fluorophenyl)phosphino]ethane]bis[chlorogold (I)]

Thiodiglycol, 2.1 g (0.017 mol) was added to a stirred solution of 2.47 g (0.006 mol) of chloroauric acid in a mixture of 10 ml water 30 ml CH₃OH. When a colorless solution resulted, 1.30 g (0.00276 mol) of 1,2-ethanediyl-bis[bis(4-fluorophenyl)phosphine], prepared as described in part a, in a mixture of 30 ml CHCl₃·30 ml CH₃OH was added dropwise with cooling. After the addition was complete, the reaction mixture was stirred an additional 30 minutes. The names product (separated solid) was removed and dried from CH₂Cl₂/CH₃OH and yielded 2.55 g with a melting point of 271°-272°.

EXAMPLE 18

μ-[1,2-Bis[Bis(3-Fluorophenyl)Phosphino]Ethane]Bis[Chlorogold (I)]

a. 1,2-Ethanediyl-bis[bis(3-fluorophenyl)phosphine]

The named product was prepared in a manner similar to the name product of Example 14a, except that 3-fluorophenyl magnesium bromide was substituted for the magnesium and 4-bromoanisole. The named product was collected as a solid from ETOH and had a melting point of 65°-68°.

b. μ-[1,2-Bis[bis(3-fluorophenyl)phosphino]ethane]bis[chlorogold(I)]

The named product was prepared in a manner similar to the name product of Example 17b, except that 1,2-ethanediyl-bis[bis(3-fluorophenyl)phosphine], prepared as described in part a, was employed as the ligand. The named product was removed from CHCl₃/CH₃OH as a solid, and had a melting point of 244°-245°.

EXAMPLE 19

μ-[1,2-Bis(Dibenzylphosphino)Ethane]Bis[Chlorogold (I)]

Thiodiglycol (2.1 g, 17.2 mmole) in methanol (15 ml) was added to chloroauric acid tetrahydrate (2 g, 4.85 mmole) in water (10 ml) kept at 0°, and stirred until colorless. Bis (1,2-dibenzylphosphino)Ethane (1.08 g, 2.43 mmole), obtained from Strem Chemical Company, in chloroform (30 ml)/methanol (10 ml) was added dropwise. After 30 minutes, the precipitate was collected, washed with methanol and recrystallized from acetonitrile to give 0.72 g (33%) of the named product (white crystals) with a melting point of 231°-232°.

EXAMPLE 20

μ-[1,2-Bis(Di-p-trifluoromethylphenylphosphino)ethane]Bis-[chlorogold(I)]

Thiodiglycol (0.4 g, 3.3 mmole) in ethanol (5 ml) was added to chloroauric acid tetrahydrate (0.61 g, 1.48 mmole) in water (15 ml) kept at 0° C., and stirred until near colorless. Bis (1,2-di-p-trifluoromethylphenylphosphino)-ethane (0.5 g, 0.74 mmole), obtained from Strem Chemical Company, in acetone (20 ml) was then added to give an oil. Water (30 ml) was added and stirring continued until the oil solidified. The precipitate was collected, washed with water and dried to give 0.68 g (81%) of off-white solid with a melting point of 285°-187°. Recrystallization from acetone/ethanol gave an analytical sample of the named product with a melting point of 295°-297°.

EXAMPLE 21

μ-[1,2-Bis(Diphenylphosphino)Ethane]Bis-[Acetatogold(I)]

A mixture of μ-[1,2-Bis(diphenylphosphino)ethane]-bis[chlorogold (I)] (0.038 g, 0.44 mmole), prepared as described in Example 1, and silver acetate (0.32 g, 1.9 mmole) in methylene chloride (25 ml) was stirred overnight at ambient temperature. The precipitate was collected and the solvent removed in vacuo. Crystallization of the residue from methylene chloride/hexane gave 0.34 g (84%) of the named compound which had a melting point of 196°-198°.

EXAMPLE 22

μ-[1,2-Bis(diphenylphosphino)ethane]Bis[trifluoromethyl-thiogold(I)]

Silver trifluoromethylthiolate (1.45 g, 6.96 mmole) in acetonitrile (200 ml) was added dropwise to a suspension of μ-[1,2-Bis(diphenylphosphino)ethane]bis[chlorogold(I)] (3.09, 3.48 mmole), prepared as described in Example 1, in chloroform (500 ml) and the mixture stirred 48 hours at ambient temperature. The silver chloride precipitate was collected, the solvent evaporated and the residue chromatographed (silica gel, chloroform) to give 2.1 g (61%) of the named compound which had a melting point of 204°-206°.

EXAMPLE 23

μ-[1,2-Bis(Diphenylphosphino)Ethane)Ethane]Bis[-Bromogold](I)]

A mixture of μ-1,2-Bis(diphenylphosphino)ethane]-bis[chlorogold(I)] (0.86 g, 1 mmole), prepared as described in Example 1, and sodium bromide (1.03 g, 10 mmole) in dimethylformamide (35 ml) and water (10 ml) was stirred 24 hours at ambient temperature (precipitate formed). Water (100 ml) was added and the mixture filtered. The collected solid was washed with water, slurried with acetone, and dried to give 0.78 g (82%) of the named compound (white product), which had a melting point of 299°-300°.

EXAMPLE 24

μ-[1,2-Bis(diphenylphosphino)ethane]Bis[thiocyanotogold) (I)]

A mixture of μ-[1,2-Bis(diphenylphosphino)ethane]-bis[chlorogold(I)] (1.09 g, 12 mmole), prepared as described in Example 1, and sodium thiocyanate (1.2 g, 15 mmole) in water (50 ml), dimethylformamide (20 ml), and chloroform (100 ml) was stirred overnight at ambient temperature. The mixture was poured into water (400 ml), the layers separated and the aqueous phase extracted with chloroform. The combined extracts were washed with water, dried (MgSO₄), filtered, and the volatile solvent removed at reduced pressure. Methylene chloride and ethanol were added and the solution cooled to −20°. The produce was collected and recrystallized from methylene chloride/ethanol to give 0.83 g (80%) of the named compound which had a melting point of 247°–248°. Note that this compound has been reported by DeStefano et al., *Inorg. Chem.*, 10, 998–1003 (1971), with a melting point of 227°–230°.

EXAMPLE 25

μ-[1,2-Bis(Diphenylphosphino)Ethanol]Bis[O-Ethyldithiocarbonatogold(I)]

A mixture of μ-[1,2-bis(diphenylphosphino)-ethane]-bis[chlorogold(I)] (1.0 g, 1.2 mmole), prepared as described in Example 1, and potassium ethyl xanthate (1.3 g, 8.1 mmole) in chloroform (50 ml)/ethanol (75 ml) was stirred overnight at ambient temperature. The solvent was removed at reduced pressure and the residue dissolved in chloroform, washed with water, dried (Na₂SO₄), filtered and the solvent removed. The residue was slurried with ethanol and then recrystallized from methylene chloride/hexane to give 0.95 g (79%) of the named gold complex which had a melting point of 158°–159°.

EXAMPLE 26

μ-[1-Diethylphosphino-2-Diphenylphosphino-Ethane]-bis-[Chlorogold(I)]

Chloroauric acid tetrahydrate (2.78 g, 6.74 mmole) in water (20 ml/methanol (60 ml) was reduced by thiodiglycol (3.5 g, 28.7 mmole) as described previously in Example 2. A solution of 1-diethylphosphino-2-diphenylphosphino ethane (1.02 g, 3.4 mmole), obtained from Strem Chemical Company, in chloroform (40 ml)/methanol (40 ml) was added and the mixture kept at 0° overnight. Water (300 ml) was added, the layers separated and the aqueous phase extracted with chloroform. The combined phases were dried (MgSO₄), filtered and the solvent removed in vacuo. Recrystallization of the residue from chloroform/ethanol gave 1.46 (56.4%), of the named gold complex which had a melting point of 186°–187°.

EXAMPLE 27

μ-[1,2-Bis(Diphenylphosphino)Ethane]Bis[Nitratosilver(I)]

The named product was prepared substantially in accordance with the procedure disclosed in *Inorg. Chim. Acta*, 8, 25 (1974), i.e. a hot solution of silver nitrate (0.85 g, 5 mmole) in ethanol (30 ml) and acetonitrile (1 ml) was added to a hot solution of 1,2-bis(diphenylphosphino)-ethane (1.0 g, 2.5 mmole), obtained from Strem Chemicals Inc., Danvers, Mass., in ethanol (30 ml) and chloroform (1 ml). Within seconds, the mixture became clear and then a precipitate began to appear (slight reflux observed). After two hours, the precipitate was collected, washed with ethanol and dried to give 1.62 g (88%) of the named silver complex which had a melting point of 238°, violent decomposition.

EXAMPLE 28

μ-[1,2-Bis(Diphenylphosphino)Ethane]Bis[Chlorocopper(I)]

The named product was prepared substantially in accordance with the procedure of Marsich et al., *J. Inorg. Nucl. Chem.*, 34, 933–946 (1972) i.e. a mixture of 1,2-bis(diphenylphosphino)ethane (1 g, 2.5 mmol), obtained from Strem Chemicals Inc., Danvers, Mass., and cuprous chloride (0.5 g, 5 mmole) in chloroform (25 ml) was refluxed for 1.5 hours, cooled to ambient temperature. Then the product was collected, washed with hot chloroform and dried to give 0.93 g (62%) of the named copper complex (white solid).

EXAMPLE 29

μ-[1,2-Bis(Diphenylphosphino)Ethane]Bis[L-2-Amino-2-Carboethoxyethylthio)Gold(I)]

Sodium hydroxide (0.186 g, 4.64 mmol) in ethanol (50 ml)/water (5 ml) was added to L-cysteine ethyl ester HCl (0.43 g, 2.32 mmol) in ethanol (45 ml), and stirred for 15 minutes. A slurry of μ-[1,2-(diphenylphosphino)ethane]bis-[chlorogold (I)] (1.0 g, 1.16 mmol), prepared as described in Example 1, in chloroform (75 ml) was added, and the mixture was stirred for 2 hours. The solvent was evaporated and the residue was dissolved in chloroform, washed with water, dried (MgSO₄), filtered and the solvent removed in vacuo. Chromatography (SiO₂, CH₂Cl₂—2% Et₂NH) of the residue gave 0.96 g (75%) of the named product as an amorphous solid.

EXAMPLE 30

μ-[1,4-Bis(Diphenylphosphino)Benzene]Bis[-Chlorogold(I)]

Chloroauric acid tetrahydrate (2.5 g, 6.06 mmole) in water (20 ml) was reduced by the addition of thiodiglycol (3.0 g, 24.6 mmole) in water (20 ml)/methanol (60 ml) at 0°. A solution of 1,4-diphenylphosphinobenzene (1.35 g, 3.0 mmole), obtained from Strem Chemicals Inc., Danvers, Mass., in chloroform (20 ml)/methanol (10 ml) was added, and the mixture was stirred for several hours. Water (200 ml) was added, and the product was extracted with CH₂Cl₂, dried (MgSO₄), filtered and the solvent removed in vacuo. Recrystallization of the residue from CH₂Cl₂/ethanol gave 2.28 g (83%) of the named product which had a melting point >300°.

EXAMPLE 31

Bis(1,2-Diphenylphosphino)Benzene

The named compound was commercially obtained from Strem Chemicals, Inc., Danvers, Mass.

EXAMPLE 32

μ-[1,2-Bis[di(phenyl-d₅)phosphino]ethane]bis-[chlorogold(I)]

a. 1,2-Ethanediyl-bis[di(phenyl-d₅)phosphine]

1,2-ethanediyl-bis[di(phenyl-d₅)phosphine] was prepared in a manner similar to the named product of Example 15a except that bromobenzene-d₅, obtained from Aldrich Chemical Co., Inc., Milwaukee, Wis., was substituted for bromopentafluorobenzene, and the reaction was carried out at 10°–15°. 1,2-ethanediyl-bis[di(phenyl-d₅)phosphine] was collected as a solid by recrystallization from ethanol, and had a melting point of 139.5°–140.5°.

b.
μ-[1,2-Bis[di(phenyl-d5)phosphino]ethane]ethane[chlorogold(I)]

The named product was prepared in a manner similar to the product of Example 17b except that 1,2-ethanediyl-bis[di(phenyl-d5)phosphine], prepared as described above, was used in place of 1,2-ethanediyl-bis[bis(4-fluorophenyl)-phosphine], and the phosphine ligand was added as a suspension in ethanol to the gold(I) solution. Recrystallization from DMF/H2O gave the named product: DMF, which had a melting point of 287.5°–289°.

EXAMPLE 33

μ-[1,2-Bis[Bis(4-Methylthiophenyl)Phosphino]ethane]-Bis[chlorogold(I)]

a.
1,2-Ethanediyl-Bis[Bis(4-methylthiophenyl)phosphine]

Using 4-bromothioanisole in place of 4-bromoanisole, the named produce was prepared in a manner similar to that of the named product in Example 14a. Residual syrup, obtained after concentration under reduced pressure, was stirred with cold acetone, solid material was removed by filtration and the named product was recrystallized from CHCl3/EtOH, and had a melting point of 147°–148°.

b.
μ-[1,2-Bis[bis(4-Methylthiophenyl)Phosphino]Ethane]-bis[Chlorogold(I)]

A solution of 8.64 g (0.021 mol) of chloroauric acid tetrahydrate in aqueous methanol (15 ml H2O/50 ml MeOH) was stirred with 10.26 g (0.084 mol) of thiodiglycol. The resulting colorless solution was diluted with 200 ml of acetone and was cooled in ice. 5.82 g (0.01 mol) of 1,2-ethanediyl-bis[bis(4-methylthiophenyl)phosphine], prepared as described above, suspended in 100 ml of methanol was added to the mixture. The reaction suspension was stirred for two hours, solid was removed and the named product was recrystallized from CHCl3/ETOH, and had a melting point of 221.5°–222°.

EXAMPLE 34

As a specific embodiment of a composition of this invention, an active ingredient, such as one part of the complex of Example 1 or one part bis(1,2-diphenylphosphino)-ethane, is dissolved in 5 parts of dimethylacetamide and 5 parts of polyethoxylated castor oil and then normal saline solution qs, and is administered parenterally in one dose of 5 mg/m² to a host animal afflicted with tumor cells sensitive to that complex.

What is claimed is:

1. A pharmaceutical composition comprising an effective tumor cell growth-inhibiting amount of an active ingredient and an inert pharmaceutically acceptable carrier or diluent, wherein said composition is useful for inhibiting the growth of animal tumor cells sensitive to the active ingredient, and wherein the active ingredient is a compound of the formula:

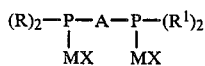

wherein
R and R¹ are the same and are phenyl; perdeuterophenyl, cyclohexyl; benzyl; pentahalophenyl, monosubstituted phenyl wherein said substituent is selected from halo, methoxy, methylthio, or trihalomethyl; or R is ethyl provided that R¹ is phenyl;
A is a straight or branched alkanediyl chain of from one to six carbon atoms, cis-vinylene or transvinylene;
M is the same and is Au(I), Au(III), Ag(I) or Cu(I); and
X is the same and is halo, nitrato, C1-6 alkylcarboxylato, thiocyanato, perfluoroalkylthio, cysteine C1-6 alkylester, or C1-6 alkyldithiocarbanato.

2. The composition of claim 1 wherein R and R¹ are the same and are phenyl; cyclohexyl; benzyl; or monosubstituted phenyl wherein said substituent is selected from halo or methylthio; A is ethane-1,2-diyl, propane-1,2-diyl, propane-1,3-diyl or cis-vinylene, M is gold(I), gold(III) or copper (I); and X is halo, acetato, thiocyanato, or trifluoromethylthio.

3. The composition of claim 2 wherein R and R¹ are the same and are phenyl or benzyl; A is ethane-1,2-diyl, propane-1,2-diyl, propane-1,3-diyl or cis-vinylene, M is gold(I) or gold(III), and X is halo, thiocyanato, trifluoromethylthio or acetato.

4. The composition of claim 3 wherein R and R¹ are the same and are phenyl, A is ethane-1,2-diyl, M is gold(I) and X is chloro or bromo.

5. The composition of claim 1 in which the composition is in dosage unit form adapted for parenteral administration.

6. The composition of claim 5 in which the parenteral dosage unit is adapted to administer 5 mg to about 20 mg/m² of body surface.

7. A method for inhibiting the growth of animal tumor cells sensitive to a compound of the formula:

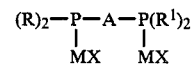

wherein:
R and R¹ are the same and are phenyl; perdeuterophenyl, cyclohexyl; benzyl; pentahalophenyl, monosubstituted phenyl wherein said substituent is selected from halo, methoxy, methylthio, or trihalomethyl; or R is ethyl provided that R¹ is phenyl;
A is a straight or branched alkanediyl chain of from one to six carbon atoms, cis-vinylene or transvinylene;
M is the same and is Au(I), Au(III), Ag(I) or Cu(I); and
X is the same and is halo, nitrato, cysteine C1-6 alkylester; C1-6 alkylcarboxylato, thiocyanato, perfluoroalkylthio, or C1-6 alkyldithiocarbanato; which comprises administering to an animal afflicted with said tumor cells an effective tumor cell growth-inhibiting amount of said compound.

8. The method of claim 7 wherein R and R¹ are the same and are phenyl; cyclohexyl; benzyl; or monosubstituted phenyl wherein said substituent is selected from halo or methylthio; A is ethane-1,2-diyl, propane-1,2-diyl, propane-1,3-diyl or cis-vinylene, M is gold(I), gold(III) or copper(I); and X is halo, acetato, thiocyanato, or trifluoromethylthio.

9. The method of claim 8 wherein R and $R^1$ are the same and are phenyl or benzyl; A is ethane-1,2-diyl, propane-1,2-diyl, propane-1,3-diyl or cis-vinylene, M is gold(I), or gold(III), and X is halo, thiocyanato, trifluoromethylthio or acetato.

10. The method of claim 9 wherein R and $R^1$ are the same and are phenyl, A is ethane-1,2-diyl, M is gold(I) and X is chloro or bromo.

11. The method of claim 7 in which the administration is parenteral and the amount is selected from the unit dose range of from about 5 mg to about 20 mg/m² of body surface administered per day for one to five days.

12. The method of claim 11 in which the administration is repeated about every fourth week for four courses of treatment.

13. The method of claim 12 in which during the course of treatment the amount administered is selected from about 300 mg to about 1000 mg.

14. A method of inhibiting the growth of animal tumor cells sensitive to μ-[1,2-bis(diphenylphosphino)-ethane]bis-[chlorogold(I)] which comprises parenterally administering to a host animal afflicted with said tumor cells a solution or suspension containing μ-[1,2-bis-(diphenylphosphino)ethane]bis[chlorogold(I)] in an amount sufficient to effectively inhibit the growth of the tumor cells.

* * * * *